United States Patent
Chen et al.

(12)

(10) Patent No.: US 11,680,252 B2
(45) Date of Patent: Jun. 20, 2023

(54) PET HYDROLASE HAVING IMPROVED THERMAL STABILITY

(71) Applicant: Hubei University, Wuhan (CN)

(72) Inventors: Chun-Chi Chen, Wuhan (CN); Jian-Wen Huang, Wuhan (CN); Xiuqin Li, Wuhan (CN); Wei Zeng, Wuhan (CN); Lilan Zhang, Wuhan (CN); Yunyun Yang, Wuhan (CN); Longhai Dai, Wuhan (CN); Jian Min, Wuhan (CN); Yu Yang, Wuhan (CN); Rey-Ting Guo, Wuhan (CN)

(73) Assignee: HUBEI UNIVERSITY, Wuhan (CN)

( * ) Notice: Subject to any disclaimer, the term of this patent is extended or adjusted under 35 U.S.C. 154(b) by 0 days.

(21) Appl. No.: 17/532,751

(22) Filed: Nov. 22, 2021

(65) Prior Publication Data
US 2022/0307000 A1 Sep. 29, 2022

(30) Foreign Application Priority Data
Mar. 25, 2021 (CN) .......................... 202110319852.7

(51) Int. Cl.
*C12N 9/88* (2006.01)
*C12N 9/18* (2006.01)

(52) U.S. Cl.
CPC ..................................... *C12N 9/18* (2013.01)

(58) Field of Classification Search
CPC ... C12N 9/18; C12N 9/52; C12N 9/14; C12N 9/16; C12N 15/74; C12P 7/22; C12Y 301/01; C12Y 301/01074
USPC ......................................................... 435/197
See application file for complete search history.

(56) References Cited

PUBLICATIONS

Devos et al., Proteins: Structure, Function and Genetics, 2000, vol. 41: 98-107.*
Witkowski et al., Biochemistry 38:11643-11650, 1999.*
Kisselev L., Structure, 2002, vol. 10: 8-9.*
Whisstock et al., Quarterly Reviews of Biophysics 2003, vol. 36 (3): 307-340.*

* cited by examiner

*Primary Examiner* — Tekchand Saidha
*Assistant Examiner* — Mohammad Y Meah
(74) *Attorney, Agent, or Firm* — Kirton McConkie; Evan R. Witt (57) ABSTRACT

A PET hydrolase having improved thermal stability is disclosed. The PET hydrolase has a modified amino acid sequence of SEQ ID NO: 2 or a modified amino acid sequence with at least 80% sequence identity of SEQ ID NO: 2, wherein the modification is a substitution of asparagine at position 248 or a corresponding position with proline.

2 Claims, 6 Drawing Sheets
Specification includes a Sequence Listing.

```
atggacggagttctctggcgagtgcgaaccgcggcgctcatggccgcgctgctcgccctcgcagcctgggcgctggtctgggcttcgccc
 M  D  G  V  L  W  G  V  R  P  A  A  L  M  A  A  L  L  A  L  A  A  W  A  L  V  W  A  S  P agcgtcgaggctcaatctaaccataccagcgtggcccaaacccaacccgttctgtctgaccgctgaaggtccattctctgttgctacc
 S  V  E  A  Q  S  N  P  Y  Q  R  G  P  N  P  T  R  S  L  T  D  G  F  S  V  A  T tacaccgtttctcgtctgtccgtgtctggtttcggtggtggtgttatctactaccctaccggtacctctctgaccttcggtggcatcgct
 Y  T  V  S  R  L  S  V  S  G  F  G  G  G  V  I  Y  Y  P  T  G  T  S  L  T  F  G  G  I  A atgtctccaggctacaccgcagacgcttcttctctggcttggctgggtcgtctgtctggcttctcaacggtttcgttgtcgtggttatcaac
 M  S  P  G  Y  T  A  D  S  S  L  A  W  L  G  R  L  S  G  F  V  V  L  V  I  N accaactcccgttcgatggcccagattctcgtgcttcccagctgtctgcagcactgaactacctgcgtacctcttctccatctgctgtt
 T  N  S  R  F  D  G  P  D  S  R  A  S  Q  L  S  A  A  L  N  Y  L  R  T  S  S  P  S  A  V cgtgctcgtctggacgctaaccgtctggcagttgctggccactctatgggtggtggtgtaccctgcgtatcgctgaacagaaccctct
 R  A  R  L  D  A  N  R  L  A  V  A  G  H  S  M  G  G  G  G  T  L  R  I  A  E  Q  N  P  S ctgaaagcagctgtgcctctgaccccttggaacaccgacaaaaccttcaacacctctgtgccggttctgatcgttggtgctgaagctgac
 L  K  A  A  V  P  L  T  P  W  N  T  D  K  T  F  N  T  S  V  P  V  L  I  V  G  A  E  A  D accgttgcaccagtttcccagcacgctatcccattctaccagaacctgccatctaccaccccaaaagtttacgttgaactgtgcaacgca
 T  V  A  P  V  S  Q  H  A  I  P  F  Y  Q  N  L  P  S  T  T  P  K  V  Y  V  E  L  C  N  A tctcacatcgctcctaactctaacaacgctgcaatctccgtttacaccatctcttggatgaaactgtgggttgataacgacacccgttac
 S  H  I  A  P  N  S  N  N  A  A  I  S  V  Y  T  I  S  W  M  K  L  W  V  D  N  D  T  R  Y cgtcagttcctgtgcaacgttaacgaccccagctctgtgcgatttccgtaccaacaacgtcactgccag   - SEQ ID NO. 1
 R  Q  F  L  C  N  V  N  D  P  A  L  C  D  F  R  T  N  N  R  C  Q         - SEQ ID NO. 2
```

FIG. 1

| Mutant | Primer Sequence |
|--------|-----------------|
| N248P  | 5'-CCTAACTCT<u>CCA</u>AACGCTGCAATCTCCGTT-3'<br>(SEQ ID NO. 3) |

PET HYDROLASE HAVING IMPROVED THERMAL STABILITY

FIELD OF THE INVENTION

The present invention relates to a PET hydrolase, and more particularly to a PET hydrolase having improved thermal stability.

BACKGROUND OF THE INVENTION

Plastic products have been widely used in many aspects of life due to its high formability and stability and bring many conveniences to human life, but the resulted white pollution has seriously threatened the global ecosystem. At present, the global annual production of synthetic plastics has exceeded 400 million tons, wherein polyethylene terephthalate (PET) is a major contributor to the white pollution. PET is composed of ester bond-linked terephthalic acid (TPA) and ethylene glycol (EG), and is highly stable and difficult to decompose. PET is often used in mineral water bottles, polyester clothes and blister packs, which causes huge amount of waste. Since it takes hundreds of years to completely decompose synthetic plastic waste in natural degrading processes, the plastic waste has been continuously accumulated in the environment and invaded the human food chains. Accordingly, the plastic waste seriously threatens the earth's ecology and the human health, and has become one of the pollution problems of global concern.

The current treatments for PET waste mainly include landfill, incineration, recycling and biodegradation. Although landfill and incineration are the simplest, the generated waste gas and water will cause secondary pollution to the environment. As to recycling, due to the economic efficiency of recycling costs and the performance issues of recycled plastics, the recycling rate remains low at the moment. The biodegradation technology (enzymatic degradation or microbial degradation) can degrade PET into small molecules, which can be further recycled to synthesize PET. Therefore, the biodegradation technology solves the problem of PET waste, and can further recycle the raw materials for PET synthesis. Currently, the biodegradation technology has gradually become a research hotspot due to its environmentally friendly features. The scientists have been looking for effective PET biodegradation methods for a long time, and now they have found PET degradation activities from esterases, lipases and cutinases, proving the possibility of PET biodegradation. For example, TfH and TfH BTA-2 from *Thermobifida fusca*, cutinase from *Saccharomonora viridis*, and lipase B from *Candida antarctica*, etc., have all been confirmed to have PET degradation activities. However, since PET is not the major reactant of the above-mentioned enzymes, the PET degradation rate is still low, resulting in low industrial application values of the above-mentioned enzymes.

In 2016, a Japanese research team reported magical bacteria named *Ideonella sakaiensis* that can "eat plastic". The bacteria can secrete a new type of PET hydrolase (IsPETase), which is able to decompose PET into small fragments of mono(2-hydroxyethyl) terephthalic acid (MHET) at 30° C., and the decomposed products can be further digested by the bacteria and finally converted into two simple molecules, terephthalic acid (TPA) and ethylene glycol (EG). Although IsPETase has relatively higher activity in degrading PET than other esterases or cutinases and has potential industrial application value, its degradation efficiency is still low, and there is still a gap from commercial applications. Thus, the scientists have also conducted a lot of subsequent researches, whether by screening new genes from nature or modifying existing enzymes, in order to find PET hydrolases that are more suitable for industrial applications.

Therefore, the present invention intends to modify an existing PET hydrolase by analyzing its protein structure and rationally designing mutations, so as to improve the thermal stability of the PET hydrolase, thereby increasing its industrial application value and potential.

SUMMARY OF THE INVENTION

An object of the present invention is to modify a PET hydrolase by means of structural analysis and site-directed mutagenesis for improving the thermal stability of the PET hydrolase and further increasing its industrial application value and potential.

According to an aspect of the present invention, there is provided a PET hydrolase having improved thermal stability. The PET hydrolase has a modified amino acid sequence of SEQ ID NO: 2 or a modified amino acid sequence with at least 80% sequence identity of SEQ ID NO: 2, wherein the modification is a substitution of asparagine at position 248 or a corresponding position with proline.

In an embodiment, the PET hydrolase has the full length amino acid sequence of SEQ ID NO: 5.

According to another aspect of the present invention, there is provided a nucleic acid encoding the aforesaid PET hydrolase, and a recombinant plasmid comprising the aforesaid nucleic acid.

The above objects and advantages of the present invention will become more readily apparent to those ordinarily skilled in the art after reviewing the following detailed description and accompanying drawings, in which:

BRIEF DESCRIPTION OF THE DRAWINGS

FIG. 1 shows the nucleotide sequence and the amino acid sequence of the LCC-ICCG;

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

It is currently known that the enzyme with the highest PET degradation activity is the leaf compost cutinase (LCC) derived from the leaf compost metagenomics, and it has been reported that its optimal temperature is ranged from 60 to 70° C. In 2020, the University of Toulouse in France cooperated with the company CARBIOS to modify the LCC into a four-mutant enzyme named LCC-ICCG which has improved thermal stability. High temperature can effectively reduce the polymerization degree of PET and increase the flexibility of PET, and thus enhance its degradation rate. Therefore, to produce PET hydrolases with heat tolerance and thermal stability is an important modification strategy. In order to further improve the thermal stability of LCC-ICCG, the present invention further analyzed the tertiary structure of the protein, and selected the amino acids with modification potential for further modification. Particularly, the present invention utilized site-directed mutagenesis to mutate asparagine (N) at position 248 of the LCC-ICCG into proline (P) to obtain the PET hydrolase with improved thermal stability. Hereinafter, the enzyme modification method and the resulting PET hydrolase with improved thermal stability will be described in detail.

First, the LCC-ICCG gene was obtained by gene synthesis, and the gene was constructed into pET32a vector using NcoI and XhoI restriction enzymes, and then the recombinant plasmid was transformed into a competent cell to obtain the LCC-ICCG recombinant plasmid.

FIG. 1 shows the nucleotide sequence and the amino acid sequence of the LCC-ICCG, wherein the LCC-ICCG gene consists of 879 base pairs (SEQ ID NO: 1) and encodes 293 amino acids (SEQ ID NO: 2).

Figure 2:
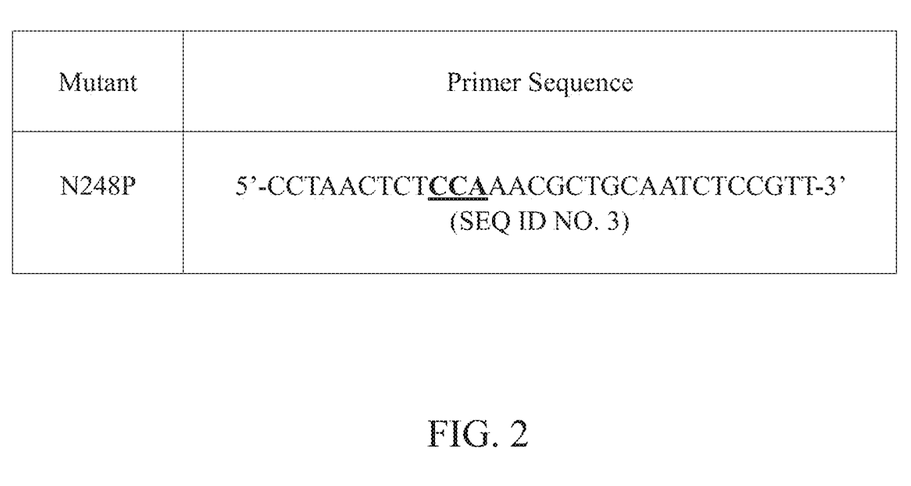
FIG. 2 shows the primer sequence for site-directed mutagenesis.
Figure 3:
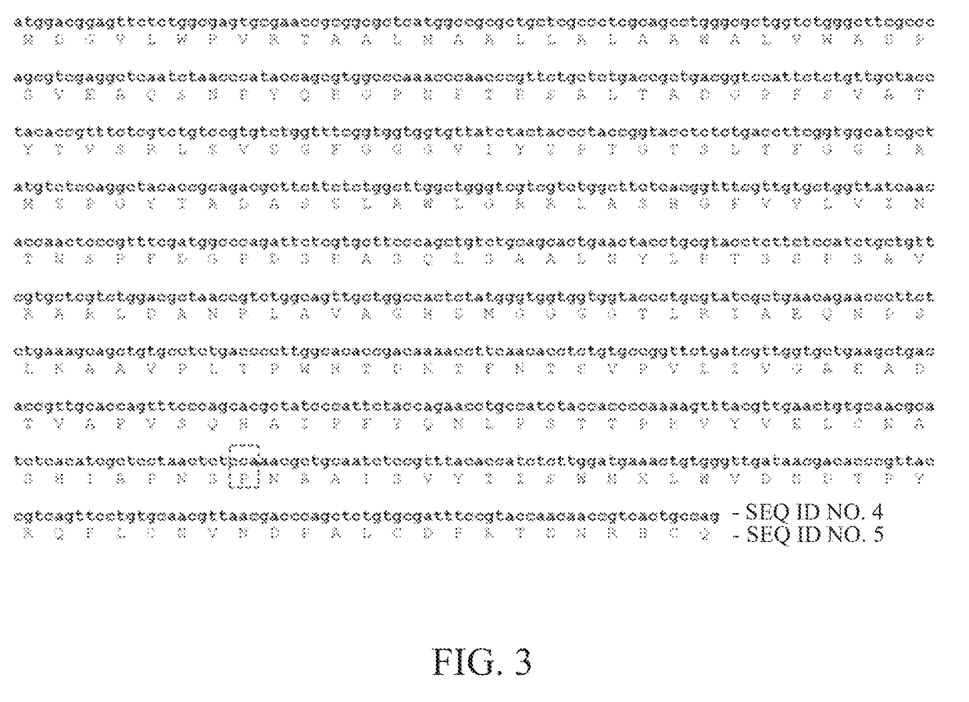
FIG. 3 shows the nucleotide sequence and the amino acid sequence of the mutant LCC-ICCG-N248P.

In order to improve the thermal stability of the LCC-ICCG, the present invention utilized site-directed mutagenesis by using the wild-type LCC-ICCG gene as the template and using the mutant primer (SEQ ID NO. 3) shown in FIG. 2 to perform the polymerase chain reaction (PCR). The original template DNA is then removed using DpnI. Subsequently, the mutant plasmid is transformed into E. coli competent cells, and the mutant gene is confirmed by DNA sequencing. Here, the present invention constructed a mutant strain N248P, which means that asparagine (N) at position 248 of LCC-ICCG was substituted with proline (P). The present invention named this mutant gene as LCC-ICCG-N248P. FIG. 3 shows the nucleotide sequence and the amino acid sequence of the mutant LCC-ICCG-N248P, wherein the LCC-ICCG-N248P gene consists of 879 base pairs (SEQ ID NO: 4) and encodes 293 amino acids (SEQ ID NO: 5).

The following is to further express the proteins in E. coli and then purify the proteins. First, the constructed recombinant plasmids LCC-ICCG and LCC-ICCG-N248P were respectively transformed into E. coli BL21 (DE3) competent cells, which were further screened in the LB culture dish containing 100 μg/ml ampicillin. Afterwards, the screened strain was inoculated into 5 ml LB and cultured overnight, then expanded to 200 ml LB medium, and finally expanded to 10 L LB medium. When the OD value reached 0.6 to 0.8, the culture temperature was cooled to 16° C. and 0.3 mM IPTG was added to induce a large amount of protein expression. After 16 hours of protein expression induction, the bacterial solution was centrifuged at 6000 rpm for 10 minutes to collect the cells. Then the bacteria were resuspended in lysis buffer (25 mM tris, 150 mM NaCl, pH 7.5), followed by disruption with a cell disruptor. Cell debris was removed by centrifugation at 16000 rpm for 30 minutes, and the supernatant was collected for the next step of purification. In order to obtain high-purity enzyme protein, the supernatant was then applied to a nickel column with a fast protein liquid chromatography (FPLC) system to elute the target protein. Later, the target protein is dialyzed in 5L buffer (25 mM Tris, 150 mM NaCl, pH 7.5) and dialyzed overnight at 4° C. At the same time, 200 μl tobacco etch virus (TEV) protease was added to digest and remove the His tag from the protein. The protein solution was applied to another nickel column, and the target protein without His tag was collected. Then the purified recombinant protein was analyzed for protein purity by polyacrylamide gel electrophoresis (SDS-PAGE).

The PET-hydrolytic activity was measured to compare the activity difference between the LCC-ICCG and the LCC-ICCG-N248P. The method for measuring the PET-hydrolytic activity is as follows. The reaction buffer contained 50 mM glycine, pH 9.0, and each reaction mixture (1 mL) included 3 mg/ml PET powder as the substrate and 10 μL enzyme (1 mg/mL). After mixing, the reaction tubes were incubated in a metal bath with agitation and the reactions were performed at different temperatures for 18 hours. Each reaction condition was performed in triplet. Afterwards, the reaction mixture was centrifuged at 12000 rpm for 10 minutes, and the supernatant was filtered through a 0.22 μm filter membrane. Then the filtered supernatant in each group was determined and analyzed by high performance liquid chromatography (HPLC) equipped with InertSustain C18 column (4.6×250 mm, 5 μm). The mobile phase was methanol/phosphate (20 mM, pH 2.5), the flow rate is 1 ml/min, the detection wavelength is 254 nm, the elution condition is 0-15 minutes, and the methanol linear gradient is 35-70%.

Figure 4:
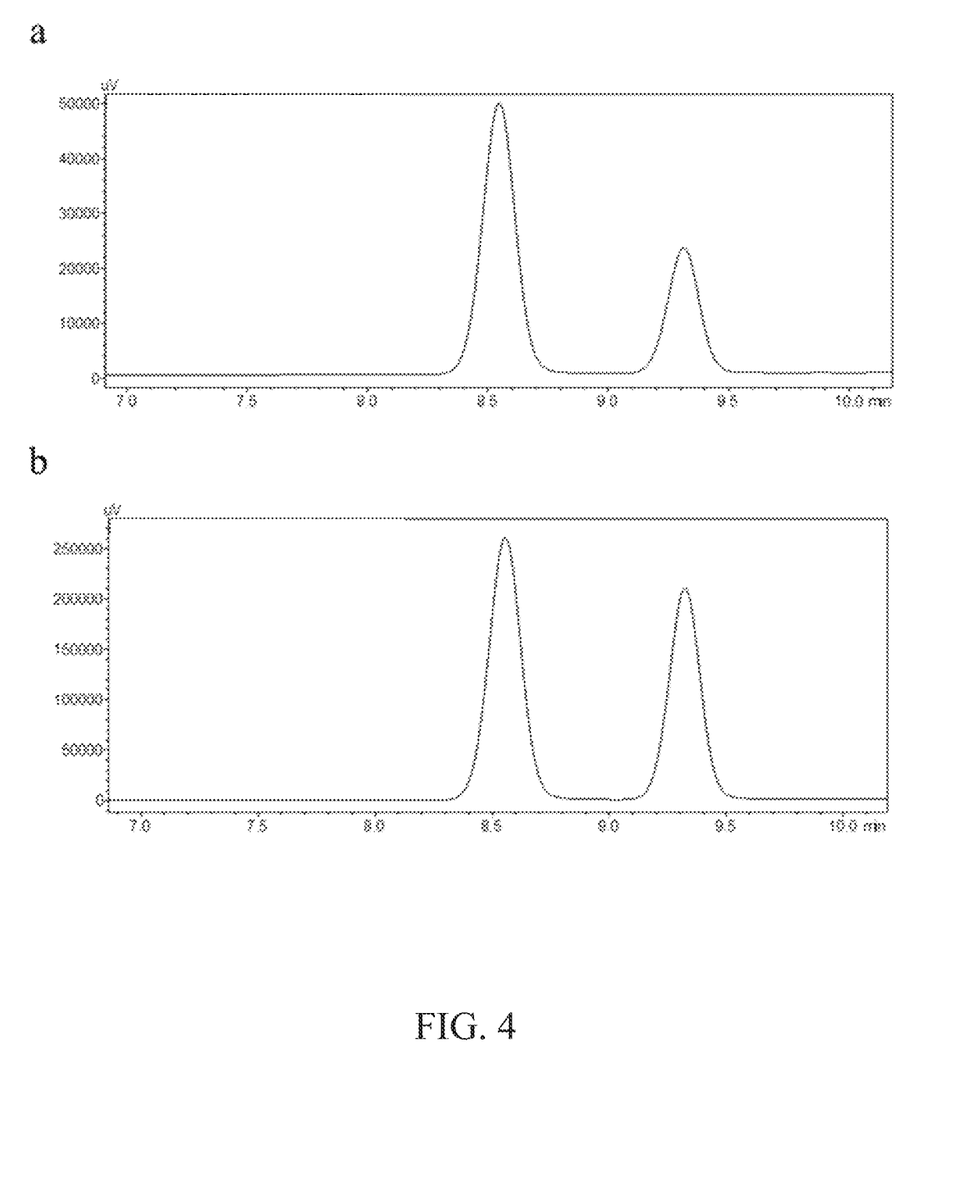
FIG. 4 shows the HPLC analysis of the PET degradation products.
Figure 5:
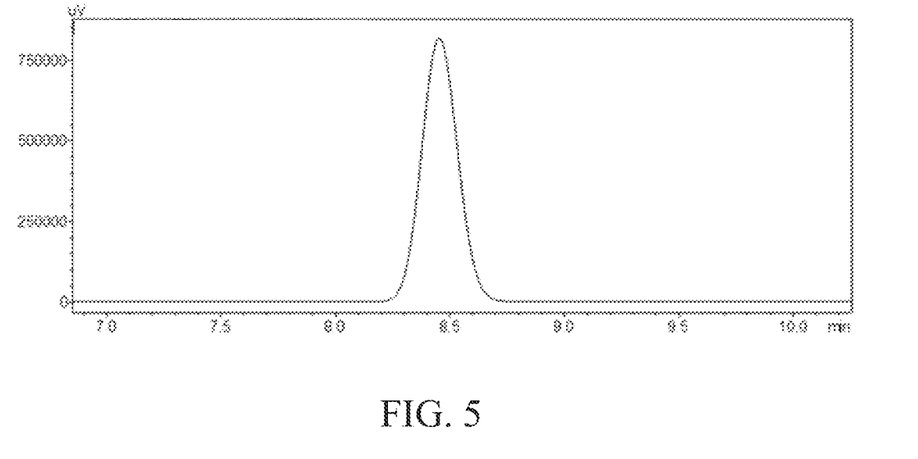
FIG. 5 shows the HPLC analysis of the standard product TPA.
Figure 6:
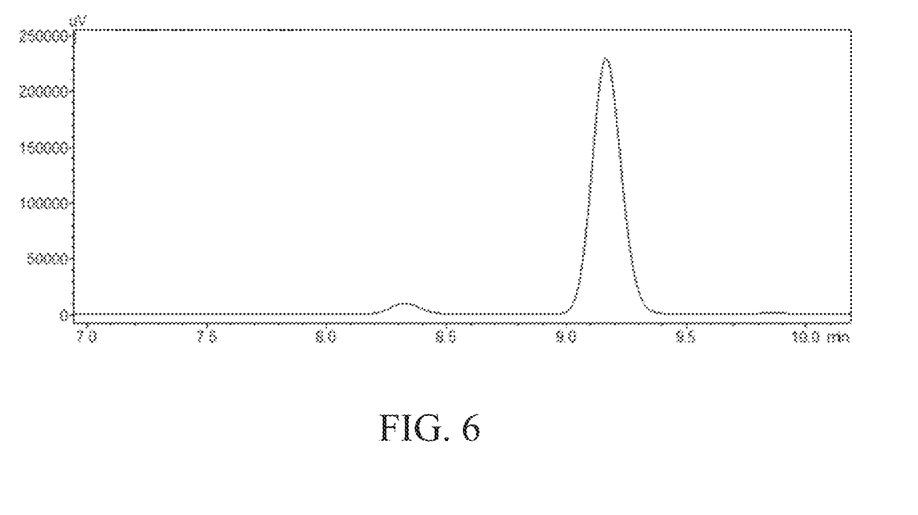
FIG. 6 shows the HPLC analysis of the standard product MHET.

FIG. 4 shows the HPLC analysis of the PET degradation products, wherein the subfigure a shows the HPLC analysis of LCC-ICCG, and the subfigure b shows the HPLC analysis of LCC-ICCG-N248P. As shown in FIG. 4, both detections peaked at a retention time of 8.55 minutes and a retention time of 9.30 minutes. The peak time with a retention time of 8.55 minutes is consistent with the standard product TPA (FIG. 5), so the substance with a retention time of 8.55 minutes is TPA. The peak time with a retention time of 9.30 minutes is consistent with the standard product MHET (FIG. 6), so the substance with a retention time of 9.30 minutes is MHET. Then, the peak areas of the degradation products MHET and TPA of LCC-ICCG and LCC-ICCG-N248P were respectively converted into product concentrations via the standard curves of MHET and TPA. The PET-hydrolytic activity was defined as the sum of the concentrations of MHET and TPA.

Figure 7:
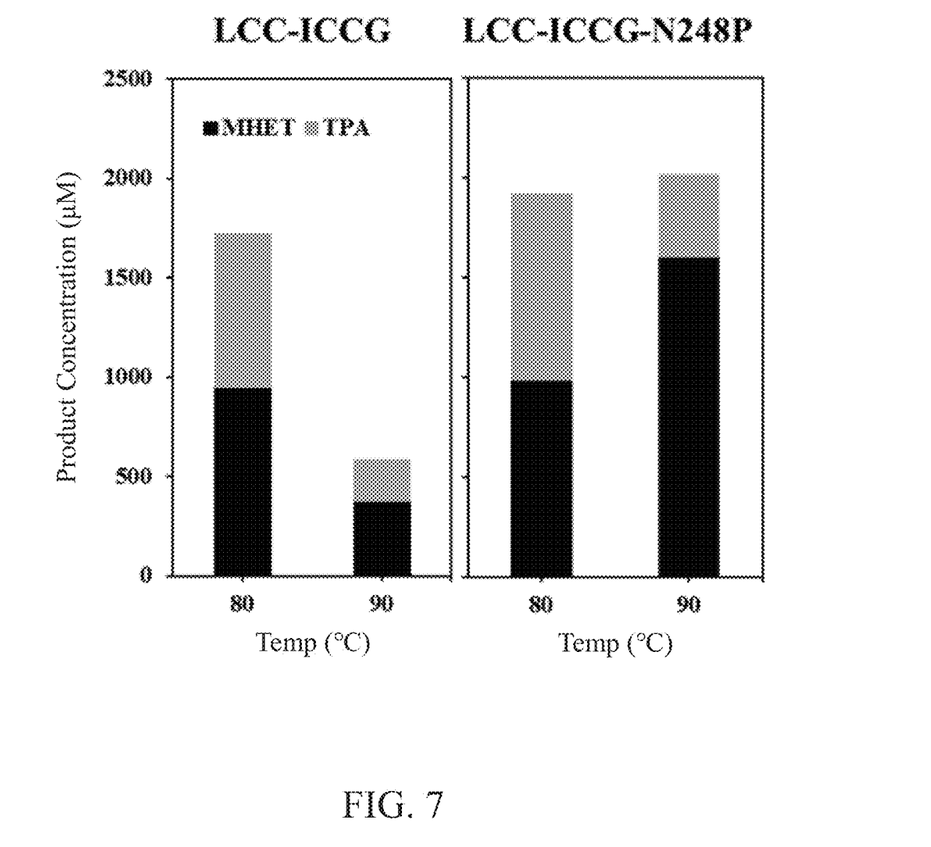
FIG. 7 shows the heat tolerance analysis of LCC-ICCG and LCC-ICCG-N248P.

FIG. 7 shows the heat tolerance analysis of LCC-ICCG and LCC-ICCG-N248P. As shown in FIG. 7, under different reaction temperature conditions (80° C. and 90° C.), the PET-hydrolytic activity of LCC-ICCG-N248P is higher than that of LCC-ICCG. The PET-hydrolytic activity of LCC-ICCG-N248P at 80° C. is 111% of that of LCC-ICCG, while the PET-hydrolytic activity of LCC-ICCG-N248P at 90° C. is 344% of that of LCC-ICCG. In addition, the PET-hydrolytic activity of LCC-ICCG decreased significantly when reacted at 90° C., while the modified LCC-ICCG-N248P still maintained considerable activity. Therefore, through the structural analysis and the rational design and modification, the present invention significantly increased the thermal stability of the PET hydrolase, and the modified LCC-ICCG-N248P successfully become a PET hydrolase with high heat tolerance, which improves its application value in the PET degradation industry, and the possibility of expanding application scope.

In conclusion, in order to modify the cutinase LCC-ICCG into a PET hydrolase having improved thermal stability, the present invention utilized structural analysis and site-directed mutagenesis to modify the LCC-ICCG, and the modified mutant LCC-ICCG-N248P (SEQ ID NO. 5) successfully improved its heat tolerance, thereby obtaining a PET hydrolase having improved thermal stability, and enhancing the industrial application value of the PET hydrolase. Besides, the enzymes usually have some variations among different species but still have the same function, and most of them have at least 80% or 90% identity in amino acid sequence. Obviously, the enzymes are allowed to have some amino acid sequence variations but still maintain the enzyme function. In other words, the sequence of the modified PET hydrolase provided in the present invention is not limited to SEQ ID NO: 5, but also includes the sequence with at least 80% or 90% sequence identity of SEQ ID NO: 2 having the substitution of asparagine at a corresponding position with proline.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A PET hydrolase having the modified amino acid sequence of SEQ ID NO: 2, wherein the modification is a substitution of asparagine at position 248 with proline of the SEQ ID NO: 2.

2. The PET hydrolase according to claim 1 having the full length amino acid sequence of SEQ ID NO: 5.

* * * * *

SEQUENCE LISTING

```
<160> NUMBER OF SEQ ID NOS: 5

<210> SEQ ID NO 1
<211> LENGTH: 879
<212> TYPE: DNA
<213> ORGANISM: Artificial Sequence
<220> FEATURE:
<223> OTHER INFORMATION: Mutant

<400> SEQUENCE: 1
atggacggag ttctctggcg agtgcgaacc gcggcgctca tggccgcgct gctcgccctc      60
gcagcctggg cgctggtctg ggcttcgccc agcgtcgagg ctcaatctaa cccataccag     120
cgtggcccaa acccaacccg ttctgctctg accgctgacg gtccattctc tgttgctacc     180
tacaccgttt ctcgtctgtc cgtgtctggt ttcggtggtg gtgttatcta ctaccctacc     240
ggtacctctc tgaccttcgg tggcatcgct atgtctccag gctacaccgc agacgcttct     300
tctctggctt ggctgggtcg tcgtctggct ctcacggttt cgttgtgct ggttatcaac     360 accaactccc gtttcgatgg cccagattct cgtgcttccc agctgtctgc agcactgaac     420
tacctgcgta cctcttctcc atctgctgtt cgtgctcgtc tggacgctaa ccgtctggca     480
gttgctggcc actctatggg tggtggtggt accctgcgta tcgctgaaca gaacccttct     540
ctgaaagcag ctgtgcctct gaccccttgg cacaccgaca aaaccttcaa cacctctgtg     600
ccggttctga tcgttggtgc tgaagctgac accgttgcac agtttcccca gcacgctatc     660
ccattctacc agaacctgcc atctaccacc ccaaaagttt acgttgaact gtgcaacgca     720
tctcacatcg ctcctaactc taacaacgct gcaatctccg tttacaccat ctcttggatg     780
aaactgtggg ttgataacga cacccgttac cgtcagttcc tgtgcaacgt taacgaccca     840
gctctgtgcg atttccgtac caacaaccgt cactgccag                             879

<210> SEQ ID NO 2
<211> LENGTH: 293
<212> TYPE: PRT
<213> ORGANISM: Artificial Sequence
<220> FEATURE:
<223> OTHER INFORMATION: Mutant

<400> SEQUENCE: 2

Met Asp Gly Val Leu Trp Arg Val Arg Thr Ala Ala Leu Met Ala Ala
1               5                   10                  15

Leu Leu Ala Leu Ala Ala Trp Ala Leu Val Trp Ala Ser Pro Ser Val
                20                  25                  30

Glu Ala Gln Ser Asn Pro Tyr Gln Arg Gly Pro Asn Pro Thr Arg Ser
            35                  40                  45

Ala Leu Thr Ala Asp Gly Pro Phe Ser Val Ala Thr Tyr Thr Val Ser
```

```
                50                  55                  60
Arg Leu Ser Val Ser Gly Phe Gly Gly Val Ile Tyr Tyr Pro Thr
 65                  70                  75                  80

Gly Thr Ser Leu Thr Phe Gly Gly Ile Ala Met Ser Pro Gly Tyr Thr
                     85                  90                  95

Ala Asp Ala Ser Ser Leu Ala Trp Leu Gly Arg Arg Leu Ala Ser His
                100                 105                 110

Gly Phe Val Val Leu Val Ile Asn Thr Asn Ser Arg Phe Asp Gly Pro
                115                 120                 125

Asp Ser Arg Ala Ser Gln Leu Ser Ala Ala Leu Asn Tyr Leu Arg Thr
            130                 135                 140

Ser Ser Pro Ser Ala Val Arg Ala Arg Leu Asp Ala Asn Arg Leu Ala
145                 150                 155                 160

Val Ala Gly His Ser Met Gly Gly Gly Thr Leu Arg Ile Ala Glu
                165                 170                 175

Gln Asn Pro Ser Leu Lys Ala Ala Val Pro Leu Thr Pro Trp His Thr
                180                 185                 190

Asp Lys Thr Phe Asn Thr Ser Val Pro Val Leu Ile Val Gly Ala Glu
                195                 200                 205

Ala Asp Thr Val Ala Pro Val Ser Gln His Ala Ile Pro Phe Tyr Gln
            210                 215                 220

Asn Leu Pro Ser Thr Thr Pro Lys Val Tyr Val Glu Leu Cys Asn Ala
225                 230                 235                 240

Ser His Ile Ala Pro Asn Ser Asn Ala Ala Ile Ser Val Tyr Thr
                245                 250                 255

Ile Ser Trp Met Lys Leu Trp Val Asp Asn Asp Thr Arg Tyr Arg Gln
                260                 265                 270

Phe Leu Cys Asn Val Asn Asp Pro Ala Leu Cys Asp Phe Arg Thr Asn
                275                 280                 285

Asn Arg His Cys Gln
    290

<210> SEQ ID NO 3
<211> LENGTH: 30
<212> TYPE: DNA
<213> ORGANISM: Artificial Sequence
<220> FEATURE:
<223> OTHER INFORMATION: Synthetically generated primer

<400> SEQUENCE: 3
cctaactctc caaacgctgc aatctccgtt                                      30

<210> SEQ ID NO 4
<211> LENGTH: 879
<212> TYPE: DNA
<213> ORGANISM: Artificial Sequence
<220> FEATURE:
<223> OTHER INFORMATION: Mutant

<400> SEQUENCE: 4
atggacggag ttctctggcg agtgcgaacc gcggcgctca tggccgcgct gctcgccctc      60
gcagcctggg cgctggtctg ggcttcgccc agcgtcgagg ctcaatctaa cccataccag     120
cgtggcccaa acccaacccg ttctgctctg accgctgacg tccattctc tgttgctacc     180 tacaccgttt ctcgtctgtc cgtgtctggt tcggtggtg gtgttatcta ctaccctacc     240
ggtacctctc tgaccttcgg tggcatcgct atgtctccag ctacaccgc agacgcttct     300
```

```
tctctggctt ggctgggtcg tcgtctggct tctcacggtt tcgttgtgct ggttatcaac    360
accaactccc gtttcgatgg cccagattct cgtgcttccc agctgtctgc agcactgaac    420
tacctgcgta cctcttctcc atctgctgtt cgtgctcgtc tggacgctaa ccgtctggca    480
gttgctggcc actctatggg tggtggtggt accctgcgta tcgctgaaca gaacccttct    540
ctgaaagcag ctgtgcctct gaccccttgg cacaccgaca aaaccttcaa cacctctgtg    600
ccggttctga tcgttggtgc tgaagctgac accgttgcac agtttccca gcacgctatc    660
ccattctacc agaacctgcc atctaccacc ccaaaagttt acgttgaact gtgcaacgca    720
tctcacatcg ctcctaactc tccaaacgct gcaatctccg tttacaccat ctcttggatg    780
aaactgtggg ttgataacga cacccgttac cgtcagttcc tgtgcaacgt taacgaccca    840
gctctgtgcg atttccgtac caacaaccgt cactgccag                           879
```

<210> SEQ ID NO 5
<211> LENGTH: 293
<212> TYPE: PRT
<213> ORGANISM: Artificial Sequence
<220> FEATURE:
<223> OTHER INFORMATION: Mutant

<400> SEQUENCE: 5

```
Met Asp Gly Val Leu Trp Arg Val Arg Thr Ala Ala Leu Met Ala Ala
1               5                   10                  15

Leu Leu Ala Leu Ala Ala Trp Ala Leu Val Trp Ala Ser Pro Ser Val
            20                  25                  30

Glu Ala Gln Ser Asn Pro Tyr Gln Arg Gly Pro Asn Pro Thr Arg Ser
        35                  40                  45

Ala Leu Thr Ala Asp Gly Pro Phe Ser Val Ala Thr Tyr Thr Val Ser
    50                  55                  60

Arg Leu Ser Val Ser Gly Phe Gly Gly Gly Val Ile Tyr Tyr Pro Thr
65                  70                  75                  80

Gly Thr Ser Leu Thr Phe Gly Gly Ile Ala Met Ser Pro Gly Tyr Thr
                85                  90                  95

Ala Asp Ala Ser Ser Leu Ala Trp Leu Gly Arg Arg Leu Ala Ser His
            100                 105                 110

Gly Phe Val Val Leu Val Ile Asn Thr Asn Ser Arg Phe Asp Gly Pro
        115                 120                 125

Asp Ser Arg Ala Ser Gln Leu Ser Ala Ala Leu Asn Tyr Leu Arg Thr
    130                 135                 140

Ser Ser Pro Ser Ala Val Arg Ala Arg Leu Asp Ala Asn Arg Leu Ala
145                 150                 155                 160

Val Ala Gly His Ser Met Gly Gly Gly Gly Thr Leu Arg Ile Ala Glu
                165                 170                 175

Gln Asn Pro Ser Leu Lys Ala Ala Val Pro Leu Thr Pro Trp His Thr
            180                 185                 190

Asp Lys Thr Phe Asn Thr Ser Val Pro Val Leu Ile Val Gly Ala Glu
        195                 200                 205

Ala Asp Thr Val Ala Pro Val Ser Gln His Ala Ile Pro Phe Tyr Gln
    210                 215                 220

Asn Leu Pro Ser Thr Thr Pro Lys Val Tyr Val Glu Leu Cys Asn Ala
225                 230                 235                 240

Ser His Ile Ala Pro Asn Ser Pro Asn Ala Ala Ile Ser Val Tyr Thr
                245                 250                 255

Ile Ser Trp Met Lys Leu Trp Val Asp Asn Asp Thr Arg Tyr Arg Gln
```

-continued

```
                260                 265                 270
Phe Leu Cys Asn Val Asn Asp Pro Ala Leu Cys Asp Phe Arg Thr Asn
            275                 280                 285

Asn Arg His Cys Gln
    290
```

(12) EX PARTE REEXAMINATION CERTIFICATE (12641st)
United States Patent
Chen et al.

(10) Number: US 11,680,252 C1
(45) Certificate Issued: Jul. 11, 2024

(54) PET HYDROLASE HAVING IMPROVED THERMAL STABILITY

(71) Applicant: Hubei University, Wuhan (CN)

(72) Inventors: Chun-Chi Chen, Wuhan (CN); Jian-Wen Huang, Wuhan (CN); Xiuqin Li, Wuhan (CN); Wei Zeng, Wuhan (CN); Lilan Zhang, Wuhan (CN); Yunyun Yang, Wuhan (CN); Longhai Dai, Wuhan (CN); Jian Min, Wuhan (CN); Yu Yang, Wuhan (CN); Rey-Ting Guo, Wuhan (CN)

(73) Assignee: HUBEI UNIVERSITY, Wuhan (CN)

Reexamination Request:
No. 90/019,297, Nov. 8, 2023

Reexamination Certificate for:
Patent No.: 11,680,252
Issued: Jun. 20, 2023
Appl. No.: 17/532,751
Filed: Nov. 22, 2021

(30) Foreign Application Priority Data

Mar. 25, 2021 (CN) .......................... 202110319852.7

(51) Int. Cl.
*C12N 9/18* (2006.01)

(52) U.S. Cl.
CPC ..................................... *C12N 9/18* (2013.01)

(58) Field of Classification Search
None
See application file for complete search history.

(56) References Cited

To view the complete listing of prior art documents cited during the proceeding for Reexamination Control Number 90/019,297, please refer to the USPTO's Patent Electronic System.

*Primary Examiner* — Padmashri Ponnaluri

(57) ABSTRACT

A PET hydrolase having improved thermal stability is disclosed. The PET hydrolase has a modified amino acid sequence of SEQ ID NO: 2 or a modified amino acid sequence with at least 80% sequence identity of SEQ ID NO: 2, wherein the modification is a substitution of asparagine at position 248 or a corresponding position with proline.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-2 are cancelled.

\* \* \* \* \*